(12) United States Patent
Vandevelde et al.

(10) Patent No.: US 11,585,800 B2
(45) Date of Patent: Feb. 21, 2023

(54) DEVICE AND METHOD FOR ANALYSIS OF MILK

(71) Applicant: BULTEH—2000 LTD, Stara Zagora (BG)

(72) Inventors: Wouter Vandevelde, Brussels (BE); Todor Tonchev Todorov, Stara Zagora (BG); Milena Ivanova Ivanova, Stara Zagora (BG); Teodora Teneva Urumova, Stara Zagora (BG); Stoyan Genchev Zagorov, Stara Zagora (BG); Georgi Dimitrov Ivanov, Stara Zagora (BG)

(73) Assignee: BULTEH—2000 LTD, Stara Zagora (BG)

( * ) Notice: Subject to any disclaimer, the term of this patent is extended or adjusted under 35 U.S.C. 154(b) by 1178 days.

(21) Appl. No.: 16/087,350

(22) PCT Filed: Jun. 13, 2016

(86) PCT No.: PCT/BG2016/000017
§ 371 (c)(1),
(2) Date: Sep. 21, 2018

(87) PCT Pub. No.: WO2017/177288
PCT Pub. Date: Oct. 19, 2017

(65) Prior Publication Data
US 2021/0208122 A1    Jul. 8, 2021

(30) Foreign Application Priority Data

Apr. 12, 2016    (BG) .................................... 112272

(51) Int. Cl.
*G01N 33/04* (2006.01)
*G01K 13/02* (2021.01)
(Continued)

(52) U.S. Cl.
CPC .......... *G01N 33/04* (2013.01); *G01K 13/026* (2021.01); *G01N 1/14* (2013.01); *G01N 27/06* (2013.01);
(Continued)

(58) Field of Classification Search
CPC .......... G01N 33/04; G01N 1/14; G01N 27/06; G01N 29/02; G01N 2291/022;
(Continued)

(56) References Cited

U.S. PATENT DOCUMENTS 3,442,623 A * 5/1969 Aegidius ................ G01N 21/25
356/414
3,841,756 A * 10/1974 Grochowicz .......... G01N 33/04
422/74

(Continued)

FOREIGN PATENT DOCUMENTS

| | | | |
|---|---|---|---|
| CN | 104977266 A | * | 10/2015 |
| RU | 88 809 U1 | | 11/2009 |
| WO | 2008/060235 A1 | | 5/2008 |

OTHER PUBLICATIONS

International Search Report and Written Opinion, dated Oct. 14, 2016, from corresponding PCT application No. PCT/BG2016/000017.

*Primary Examiner* — Marrit Eyassu
(74) *Attorney, Agent, or Firm* — Nixon & Vanderhye

(57) ABSTRACT

This device and method can be used for monitoring and control of the milk quality, monitoring and control of the health of dairy animal and herd management and decision-making. The device for milk analysis is composed of tanks for water and reagent, a milk probe, a unit for analysis and management and a unit for transfer and monitoring with software applications. The samples are mixed in a mixing flask, previously subjected to an ultrasonic and temperature measurement as well as a measurement of conductivity. The (Continued)

movement of the fluid through the system is performed by peristaltic pumps. The actual measurement takes place at the outflow of the measured sample in one of two funnels with elongated ends with integrated capillary of the ends of each. To the funnels are mounted a pair of motion sensors.

9 Claims, 2 Drawing Sheets

(51) Int. Cl.
*G01N 1/14* (2006.01)
*G01N 27/06* (2006.01)
*G01N 29/02* (2006.01)

(52) U.S. Cl.
CPC ....... *G01N 29/02* (2013.01); *G01N 2291/022* (2013.01)

(58) Field of Classification Search
CPC .... G01N 21/3577; G01N 33/06; G01N 33/02; G01K 13/026; A01J 5/0137; A01J 5/0135; B01L 2200/141
USPC .......................................................... 436/23
See application file for complete search history.

(56) References Cited

U.S. PATENT DOCUMENTS

| | | | |
|---|---|---|---|
| 6,297,505 B1 | 10/2001 | Frandsen et al. | |
| 7,416,822 B2 | 8/2008 | Kanada et al. | |
| 9,297,763 B2 * | 3/2016 | Heller | G01N 21/6486 |
| 2005/0123948 A1 * | 6/2005 | Claycomb | A01J 5/0131 |
| | | | 604/500 |
| 2011/0154890 A1 | 6/2011 | Holm et al. | |
| 2012/0086938 A1 | 4/2012 | Folkenberg | |
| 2013/0228690 A1 | 9/2013 | Juhl | |

* cited by examiner

DEVICE AND METHOD FOR ANALYSIS OF MILK

FIELD OF THE INVENTION

The present invention relates to a device and method for milk analyzing for a simultaneous determination of physicochemical parameters and somatic cells count, and for an indication of impurities in the milk. This device and the method can be used for measurements at milk collecting points, milk-processing enterprises as well as for measurements and control by the supervisory bodies. The invention can be used in farms for dairy animals to establish the initial parameters of the produced milk. Another field of utilization is the monitoring and control of the health of dairy animal herds, with the possibility of feedback and indication of the prescribed veterinary measures—prescription of nutritional recipes, medication treatment etc. as well as remote control of the location and the condition of the apparatus the measurements are taken with.

BACKGROUND OF THE INVENTION

There is a device for counting of somatic cells in the milk, which is composed of a milk sample receiver, milk sample pipes, along which there are pumps and a series of valves, a control panel and a funnel, all interconnected in a certain order. The funnel is connected to a container of dye and to a measuring pipe with a transparent part, which is a measuring chamber; the transparent part is pushed through a capture camera and a light source. This device measures the somatic cells in the sample of milk by photo shooting. The sample is stained in advance, then it passes through the transparent part of the pipe. In the area between the light source and the capture camera an emitted beam light is transmitted through the sample, a shooting of at least one received image is carried out, followed by the image recording and the image analysis in the controlling unit. Then the system is cleaned by cleaning fluid and it counts the somatic cells again by the re-captured, cleaned transparent part of the pipe/measuring chamber. The cleaning of the system after working cycle occurs automatically, and this step is part of the method of analysis.

There is a method for counting of somatic cells in the milk, wherein the milk and a reagent, pre-warmed from 18° C. to 22° C., are manually metered—a milk sample with a reagent in a ratio of 10 ml/5 ml, which are manually placed into a flask with a special shape. The whole is stirred 10 times for 30 s, as the stirring flask is shaken at ±90° C., after which the mixture runs through a capillary, mounted in the one end of the flask, into a measuring container, wherein the weight change of the mixture is measured, and the measured value enters the control processor for analysis, followed by a results report. The system must be washed manually for a new measurement cycle.

A known device for determination of somatic cells in the milk operates as described above and consists of a special shaped mixing flask, which is constituted by a spherical chamber for mixing, with one extended end and an embedded capillary on it. This flask is a part of a mixing system, composited of a disk and a motor, which are equipped with an optical sensor and indicators. Under the flask with the capillary is located a measuring container, below which is housed a strain gauge, connected with a processor. The device operates as follows: a milk sample and a reagent are added by hand, previously tempered and in a ratio of 10 ml/5 ml into the mixing flask. The mixing system blends the two components by shaking 10 times, and 30 s, under ±90° C. The stirred mixture runs into a container in the one end of the flask, in which is embedded a capillary. The strain gauge, placed under the container, measures the variation of the weight of the mixed sample (leaked fluid) and sends the report in the processor for evaluation. So, the described device measures the somatic cells in the milk sample/reagent through preliminary sample preparation, tempering and measuring the components of the sample in a certain ratio (outside the unit) by reporting the change of weight of the sample and performing calculations on predetermined algorithm in the processor of the device.

Some disadvantages of the known devices and methods are the lack of the possibility of a complex, multi-functional analysis of a milk sample, of the establishment of one or several physical and mechanical parameters of the sample, simultaneously with the establishment of the number of the somatic cells, no automatic dispensing of the milk and the reagent before measurement and no dosing in amounts that would help to reduce the measurement time without reducing the quality of the analysis. Another weaknesses are the higher energy consumption for the preliminary preparation of the sample components which must be measured (tempering) and no opportunity to measure in wide temperature range (according to the ambient temperature during the measurement) as well as the lack of precise and controlled filtration of the fluid in the measurement system. The measured values have a low degree of precision and accuracy of the final report, so the results can vary in large range and errors are possible. There is a lack of a next-step analysis of the data, no monitoring and without any control of the condition of the dairy animals through measuring of their milk quality.

The task of the new invention is to present a new device and method for complex multifunctional milk analysis, where on the same time both as at least one physicochemical parameter and the number of the somatic cells in the milk are measured. This device and method determine the milk quality and detect impurities in large temperature range without preheating and by automated dosing of the participating fluids in the measurement (minimum necessary to implement the measure). A precise report of the measured data with high accuracy level is achieved, with the possibility of wireless transfer of the measured and further processed data to the software applications of the monitoring devices, in order to implement automatic monitoring and control of dairy animal herds, their milk and of the status, performance and location of the device itself.

SUMMARY OF THE INVENTION

The task of the invention is solved by a device for the analysis of milk, which is composited by a milk probe and two tanks for a reagent and for water, equipped with level sensors. The level sensors are connected to the unit for analysis and control. Every of the two tanks and the milk probe are connected with separate independent pipes with the mixing flask so that the outputs of the pipes end in the mixing flask. At the beginning of each of the three pipes after the tanks and the probe is situated a peristaltic pump with a filter on its entrance. The three peristaltic pumps have a two-way connection to the unit for analysis and control. Through the milk pipe, after the pump, are arranged sequentially one after another, an ultrasound module and a conductivity sensor, each of them is also connected with the unit for analysis and control, where the connection of the ultrasonic module is bidirectional. On the milk pipe, after the conductivity sensor and on the reagent pipe after the peristaltic pump are situated temperature sensors, which are connected to the unit for analysis and control. The ends of the three pipes finish together in the mixing flask, situated in a mixing unit, which is bidirectionally connected to the unit for analysis and control. Two funnels with extended ends and capillaries on them with orifices respectively ø 1.5 mm±0.15 mm for the first funnel and ø 1.5 mm±0.3 mm for the other one are mounted after the mixing unit. To the extended end of each of the funnels are mounted a pair of motion sensors, which are connected with the unit for analysis and control. The unit for analysis and control is bidirectionally connected with the transfer unit with monitoring function;

The problem of the invention is solved by a method for milk analysis, which the above mentioned device uses and it takes place as follows:

The peristaltic pumps suck and filter the milk and the reagent simultaneously and in a ratio, which depends on the type and concentration of the reagent.

In the time that the milk needs to move from the milk probe to the mixing flask and the reagent needs form the reagent tank to the mixing flask the temperature is measured, which the both components have by entering the mixing flask.

Depending on these measurements, made by temperature sensors, the unit for analysis and control performs temperature compensation, which participates later in the analysis and processing of the milk characteristics in order to reach an accurate final report of the measured somatic cells.

After the measurement of the set amount of milk in the mixing flask the pump stops to work, the milk stops its movement in the pipe, so it can be examined by the ultrasonic module for up to 38 seconds. The needed time depends on the type of the ultrasonic module. The unit for analysis and control receives the measured data.

At the same time the conductivity of the still milk is measured in the zone of the conductivity sensor on the pipe. These data are received by the unit for analysis and control too.

The set amount of milk is shaken 5 to 12 times, for 30 seconds in 145 degree Celsius in the mixing flask by the mixing unit.

The mixture outflows through a funnel with an capillary with a diameter Ø 1.5 mm, ±0.15 mm, which is mounted on the end of the funnel and the time of expiry is measured by a pair of motion sensors by establishing the beginning and the end of the outflow.

In case that the flow is stopped by too high number of somatic cells in the milk or for another reason, the motion sensors send a signal to the unit for analysis and control, which detects that the number of the somatic cells is above the measuring range and that the capillary, through which the milk will outflow, needs a special cleaning procedure, so the measurement is repeated in the second funnel.

The collected data from the motion sensors are sent for processing and testing to the unit for analysis and control to give a final report about the number of somatic cells in the milk.

The collected data from the conductivity sensor and the ultrasonic module are sent for processing and analysis by the unit for analysis and control to give a final report about the measured parameters—at least one physicochemical parameter and a possible presence of impurities in the milk.

After expiration of the sample through the capillary of the funnel, the system is washed with water.

The transfer unit with monitoring function analyzes, archives and sends the final measured values, processed by the unit for analysis and control, wirelessly to monitoring platforms and software applications;

The advantages of the device and the method consist in the opportunity for complex and multi-functional analysis of milk, while at the same time at least one physicochemical parameter of the milk, the availability of impurities therein, as well as the number of somatic cells in the sample are measured with an ability to perform measurements without prior manual preparation and tempering of the sample. The measurement can be carried out in wide temperature ranges and with an automated dosing (minimum necessary dosage to implement the measure) of the participating fluids. The collected results can be sent wirelessly to software applications and platforms in order to control the dairy animal herds and to monitor their health status, the quality of the produced milk and the status of the device, performing the measurement.

EMBODIMENT OF THE INVENTION

Figure 1:
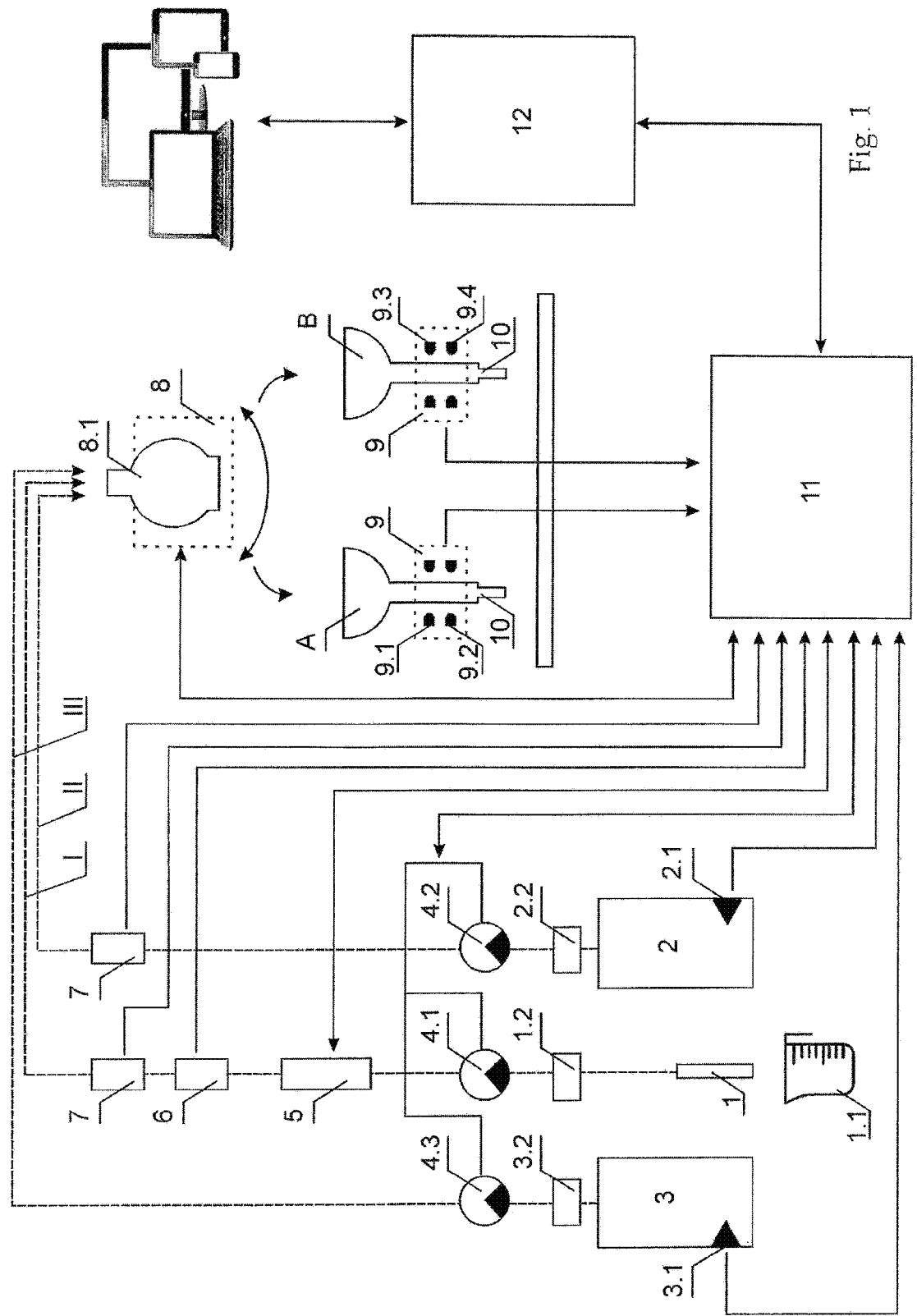
FIG. 1: shows a diagram of a device for milk analyzing
Figure 2:
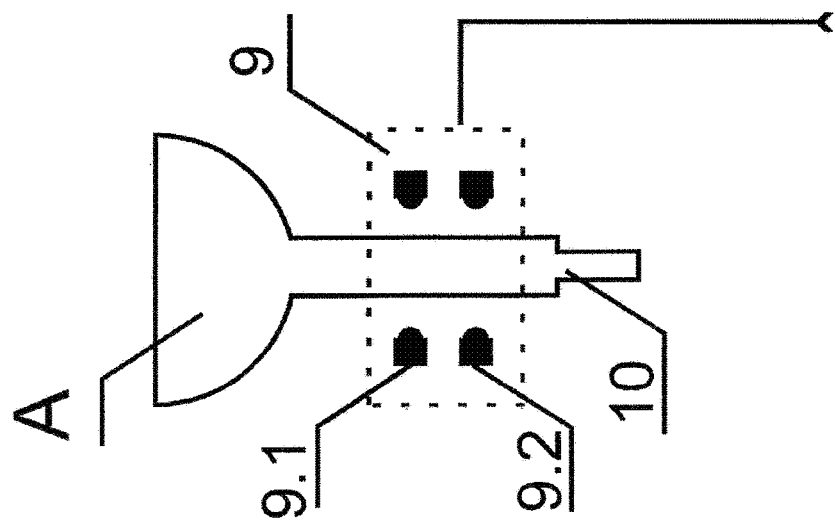
FIG. 2: shows a measuring funnel with integrated capillary and a pair of installed motion sensors in the straight part of the funnel.

A device and a method for analyzing milk is provided for a simultaneous determination of physicochemical parameters, of the number of somatic cells in the milk and for indication of impurities, which comprises:

A milk probe 1, a reagent tank 2, equipped with a level sensor 2.1 and a water tank 3, also provided with a level sensor 3.1. Each of the probe 1 and the tanks 2 and 3 are connected with a separate pipe I, II and III, the outputs of which band together in a mixing flask 8.1, located in a mixing unit 8. At the beginning of each pipe-I, II and III, after the milk probe 1 and tanks 2 and 3 are mounted peristaltic pumps 4.1, 4.2 and 4.3, which are connected bidirectionally with the unit for analysis and control 11. On the entry of each of the pumps are located filters 1.2, 2.2 and 3.2. Filters 1.2, 2.2 and 3.2 may have an automatic regulation and can be self-cleaning.

Through a pipe I after the pump 4.1 is mounted an ultrasonic module 5, after which is mounted a conductivity sensor 6, each of them is also connected to a unit for analysis and control 11, where the connection of the ultrasonic module 5 to the unit for analysis and control 11 is bidirectional. Through the pipe I after the conductivity on sensor 6 and also on the pipe II, after a pump 4.2, are mounted temperature sensors 7, both are connected to the unit for analysis and control 11. The mixing unit 8 is also bidirectionally connected with the unit for analysis and control 11. After the mixing unit 8 are arranged two funnels with extended ends A and B, the end of each of them ends with an integrated capillary 10 and to the each of the extended ends are mounted a pair of motion sensors 9, which are infrared motion sensors in this case. The capillary 10 of the funnel A has a diameter of Ø 1.5 mm U±0.15 mm and the capillary 10 of the funnel B has a diameter of the aperture Ø1.5 mm±0.3 mm. A pair of motion sensors 9 of the funnel A, consist of sensors 9.1 and 9.2, and of the funnel, of 9.3 and 9.4. Sensors 9.1, 9.2, 9.3, 9.4 may be infrared sensors or another technology can be used. Each of the sensors 9.1, 9.2, 9.3, 9.4 is connected to the unit for analysis and control 11, which in turn is connected to a transfer unit with monitoring function 12.

The performance of the device according to the invention can be described as follows: The milk probe 1 is plunged in a container of milk 1.1. In tank 2 is placed a reagent; a level senor 2.1 tracks a sufficient level of it. The level sensor 2.1, signalizes to the unit for analysis and control 11, when the reagent level in tank 2 falls below the necessary volume. When the reagent has the needed level the peristaltic pumps 4.1 and 4.2 go active. When this action starts, the fluids are already filtered by filters 1.2 and 2.2 and the milk and the reagent are dispensed at a specific ratio 2/1 so that there is a 15 ml measured fluid upon mixing in a mixing flask 8.1, through the pipes I and II. In case of impurities and obstruction of the filters, the unit for analysis and control 11 receives a signal, so that the circulation shall be suspended until the malfunction is eliminated. When the milk flows through the pipe I, its electrical conductivity is measured by the conductivity sensor 6. The data enters the unit for analysis and control 11. According to results, measured by the conductivity sensor 6, the unit for analysis and control 11 determines the presence of impurities in milk. The milk and the reagent flow through the pipes I and II and pass through temperature sensors 7, where their actual temperature is measured and sent to the unit for analysis and control 11. Depending on the reported temperatures some temperature compensations can be set by the software, which analyzes and processes the reports of the measuring elements of this device.

The purpose is to achieve a correction of the final report, to obtain precise and accurate results about the number of the somatic cells in the milk without treatment of the milk and the reagent in advance. The measurements by the conductivity sensor 6 and by the temperature sensors 7 are performed when the milk and the reagent flow in the flask 8.1, where they are mixed. After dosing of the amount of 15 ml, in a ratio 2/1 milk and a reagent, which is provided by peristaltic pumps, 4.1 and 4.2 with high precision, the pumps stop their performance, so the milk stands still in the pipe and the ultrasonic measuring of the milk starts in the zone of the ultrasonic module 5. The measurement takes 38 s from the beginning of the process and depends on the number of the measured physicochemical parameters, such as fat, non-fat solids, temperature, etc., as well as on the type of used ultrasonic module 5. After the mixing in a mixing flask 8.1 by the mixing unit 8, the mixture is shaken 10 times for about 30 s, of 145° C. The stirred mixture flows through a funnel A or B. Usually, the outflow begins in the funnel A and if it doesn't run properly or doesn't occur at all, resulted by a large number of somatic cells in the fluid or for other reasons, the infrared motion sensors 9.1 and 9.2 give an indication to the unit for analysis and control 11, the cycle is suspended, the system is washed automatically by the pump 4.3 and the cycle is renewed by pouring of the proportioned milk and reagent in a funnel B, while a funnel A can be prepared for a new measurement. A reverse sequence of work of the two funnels is possible. Being in the funnel, the mixture flows through a capillary 10. When a milk/reagent mixture flows in the extended end of the funnel, a motion sensor (infrared sensor) 9.2 reports the beginning of the outflow and a motion sensor (infrared sensor) 9.1 reports the end of the outflow, which passes through the capillary. The information is sent to the unit for analysis and control 11, which records the outflow constantly. After the outflow of the measured sample through a funnel A or B, and the completion of the data processing in the unit for analysis and control 11 the system is washed with water from tank 3 through a pump 4.3, so it is ready for a new measurement.

When a certain number of cycles are reached, the filters are cleaned. The received reports in the unit for analysis and control 11 are processed by software, where the results are immediately displayed and/or sent to the transfer unit with monitoring function 12. The transfer unit with monitoring function 12 processes and archives samples and transfers the reports and the made conclusions about the health of the dairy animals which the samples have been taken from, wirelessly to software applications in order to monitor and control the dairy animal herds. The transfer unit with monitoring function 12 sends some recommended measures for the improvement of the dairy animal care on the basis of the processed data to software applications and platforms. The transfer unit with monitoring function 12 can send also data about the location and the condition of the device to the software applications.

USE OF THE INVENTION

The invention can be used for measurements at the milk collecting points, milk-processing enterprises, as well as for measurements by the supervisory bodies to control the quality of milk products. The invention is used in farms for dairy animals to establish the initial parameters of the produced milk. The invention is used for monitoring and control of the health of the dairy animal herds, with the possibility of feedback, indicating the prescribed veterinary measures—a prescription of recipes for nutrition, treatment with medication and so on.

REFERENCES

1. PCT—WO2008/060 235;
2. A utility model RU 88809.

The invention claimed is:
1. A device for analysis of milk consisting of;
 a milk probe;
 a tank for reagent; and
 a tank for water,
 wherein the tanks are equipped with sensors for level measurement,
 wherein the tanks and the milk probe are connected to a mixing flask (8.1) by respective separate pipes for milk (I) for reagent (II) and for water (III),
 wherein the pipes have pumps thereon, the pipes with pumps thereon being situated after the milk probe and after the tanks,
 wherein the mixing flask (8.1) is placed in a mixing unit that is connected with a unit for analysis and control,
 wherein one end of the mixing flask (8.1) is extended with a built-in capillary,
 wherein each of the pumps have a filter (1.2) (2.2) and (3.2), installed at an entrance of the pumps, as each pair pump/filter is connected bidirectionally with the unit for analysis and control (11) and each pair pump/filter is mounted on the respective separate pipe for milk (I) for reagent (II) and for water (III), whose input ends are starting respectively from the milk probe (1), from the reagent tank (2) and from the water tank (3) and the ends of the pipes (I), (II) and (III) finish into the mixing flask (8.1),
 wherein on the respective separate pipe for milk (I) after the pump (4.1) are arranged sequentially one after another, an ultrasonic module (5) and a conductivity sensor (6), each of the ultrasonic module and the conductivity sensor is also connected with the unit for analysis and control (11), where a connection of the ultrasonic module (5) is bidirectional, wherein on the respective separate pipe for milk (I) after the conductivity sensor (6) and on the respective separate pipe for reagent (II) after the pump (4.2), are situated temperature sensors (7), each of the temperature sensors is connected to the unit for analysis and control (11), wherein after the mixing flask (8.1) there are two funnels (A) and (B) with elongated ends, each of the elongated ends is equipped with a capillary (10) with apertures respectively having diameters of 1.5 mm±0.15 mm for funnel (A) and 1.5 mm±0.3 mm for funnel (B), and on the elongated ends of each of the funnels, before the capillaries (10), are mounted a pair of motion sensors (9.1 and 9.2), (9.3 and 9.4) which are connected to the unit for analysis and control (11), and wherein the unit for analysis and control (11) is connected bidirectionally with a transfer unit with monitoring function (12).

2. Device according to claim 1, wherein the filters (1.2), (2.2) and (3.2) are self-cleaning.

3. Device according to claim 1, wherein the pumps (4.1), (4.2) and (4.3) are peristaktic.

4. Device according to claim 1, wherein the motion sensors (9.1), (9.2), (9.3) and (9.4) are infrared.

5. A method for analyzing milk consisting of;

an automatic dosing of the milk with reagent in ratio 2/1, and homogenization of the milk and the reagent by mixing for about 30 seconds in ±90° C. and an outflow of the homogenized mixture through a capillary, wherein the dosing of milk and reagent is performed automatically and simultaneously by peristaltic pumps (4.1) and (4.2), which are controlled by a unit for analysis and control (11), which doses the milk and the reagent in a ratio, depending on a type and concentration of the reagent, wherein the dosing is preceded by filtration through filters (1.2) and (2.2), wherein during a time that the milk needs to move from a milk probe plunged in a container of milk to a mixing flask (8.1) and the during a time that the reagent needs to move from a reagent tank to the mixing flask (8.1), measuring temperature of an incoming sample of milk and the reagent by temperature sensors (7), where depending on the measured temperature data, the unit for analysis and control (11) makes temperature compensation, wherein the temperature compensation participates in the analysis and processing of the measured temperature data for achieving of an accurate final report of number of somatic cells, wherein after achieving the accurate final report, quantity of milk in the mixing flask (8.1) when the pump (4.1) stops operation, and the milk in a pipe for milk (I) stands still, the milk in the pipe for milk in the area of an ultrasonic module (5) is subjected to testing for a time up to 38 seconds, which is depending on a type of the ultrasonic module (5), and recorded data are sent to the unit for analysis and control (11), wherein simultaneously with the ultrasonic testing, the milk in the pipe for milk (I) in the area of a conductivity sensor (6), is subjected to testing and recording an electrical conductivity of the milk and the recorded data are sent to the unit for analysis and control (11), wherein while homogenizing, the mixture is shaken to 145° C. into the mixing flask (8.1), through a mixing unit (8), and, after completion of the homogenization, the mixture is poured from the mixing flask (8.1) into a funnel (A), wherein it flows through a capillary (10) with aperture having a diameter of 1.5 mm±0.15 mm, wherein a time of outflow through funnel A is measured by a pair of motion sensors (9.1 and 9.2), the pair of motion sensors respectively by establishing the beginning and the end of outflow, and collecting and sending data for evaluation to the unit for analysis and control (11), the unit for analysis and control giving a final report about the number of somatic cells in the milk, as well as about the data from the conductivity sensor (6) and the ultrasound module (5), which are also sent for processing and analysis by the unit for analysis and control (11) to obtain a comprehensive final report on the measured parameters, at least one physicochemical parameter, and an indication of possible impurities in the milk, wherein final processed values of the comprehensive final report are analyzed, archived and sent wirelessly to monitoring platforms and software applications by a transfer unit with monitoring function (12).

6. Method according to claim 5, wherein duration and type of cleaning of filter (1.2) and (2.2) are defined automatically by the unit for analysis and control (11) depending on the type of the reagent and on the data about quality of the milk in a database, collected in last 100 measured samples.

7. Method according to claim 5, wherein in case that the outflow through a funnel (A) is disturbed by a too large number of somatic cells of the milk or for another reason, through motion sensors (9.1) and (9.2) the unit for analysis and control registers an increase of somatic cells, so a cycle is interrupted and a second measurement is started through funnel (B), with an embedded capillary (10) in the end of it, with aperture having a diameter of 1.5 mm±0.3 mm, through which the mixture runs, as a result of a second cycle of mixing, where the funnel (A) is subjected to an emergency washing.

8. Method according to claim 5, wherein the automatic dosing of milk and reagent is made in ratio 1/1, 3/1, 4/1, where the ratio is determined by the unit for analysis and control (11) and depends on the type and the concentration of the reagent.

9. Method according to claim 5, wherein the measurement of the conductivity of the milk and the recording of the measured data in the unit for analysis and control (11) begins after accomplishment of the ultrasonic measurement.

\* \* \* \* \*